US00PP36904P2

(12) United States Plant Patent
Grazzini

(10) Patent No.: US PP36,904 P2
(45) Date of Patent: Aug. 26, 2025

(54) ***AGASTACHE* PLANT NAMED 'G19131'**

(50) Latin Name: *Agastache hybrida*
Varietal Denomination: G19131

(71) Applicant: Richard A. Grazzini, Columbus, OH (US)

(72) Inventor: Richard A. Grazzini, Columbus, OH (US)

(73) Assignee: GARDEN GENETICS LLC, Columbus, OH (US)

( * ) Notice: Subject to any disclaimer, the term of this patent is extended or adjusted under 35 U.S.C. 154(b) by 0 days.

(21) Appl. No.: 18/755,328

(22) Filed: Jun. 26, 2024

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./399
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Agastache* plant named 'G19131', characterized by its relatively compact, broadly upright to somewhat outwardly spreading plant habit; vigorous growth habit and rapid growth rate; freely branching habit; dense and bushy appearance; dark green-colored leaves; freely flowering habit; compact and dense inflorescences with numerous coral red-colored flowers; and good garden performance.

2 Drawing Sheets

Figure 1:
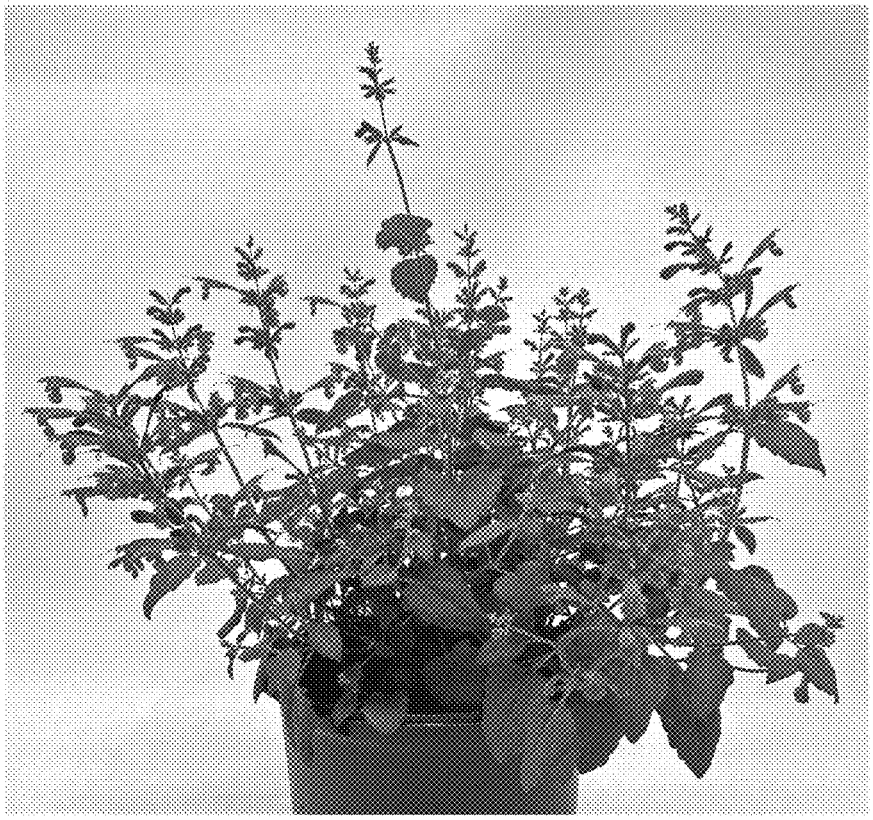

Botanical designation: *Agastache hybrida.*
Cultivar denomination: 'G19131'.

BACKGROUND OF THE INVENTION

The present invention relates to a new and distinct cultivar of *Agastache* plant, botanically known as *Agastache hybrida*, commonly referred to as Giant Hyssop or Hummingbird Mint and hereinafter referred to by the name 'G19131'.

The new *Agastache* plant is a product of a planned breeding program conducted by the Inventor in Bellefonte, Pennsylvania. The objective of the breeding program is to create new compact and dense *Agastache* plants with good summer performance and winter hardiness.

The new *Agastache* plant originated from a self-pollination in Bellefonte, Pennsylvania during the summer of 2018 of a proprietary selection of *Agastache hybrida* identified as code number 50867-1, not patented. The new *Agastache* plant was discovered and selected by the Inventor as a single flowering plant from within the progeny of the stated self-pollination in a controlled environment in Bellefonte, Pennsylvania in August, 2019.

Asexual reproduction of the new cultivar by vegetative cuttings in a controlled environment in Bellefonte, Pennsylvania since August, 2019 has shown that the unique features of this new *Agastache* plant are stable and reproduced true to type in successive generations.

SUMMARY OF THE INVENTION

Plants of the new *Agastache* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G19131'. These characteristics in combination distinguish 'G19131' as a new and distinct *Agastache* plant:

1. Relatively compact, broadly upright to somewhat outwardly spreading plant habit.
2. Vigorous growth habit and rapid growth rate.
3. Freely branching habit; dense and bushy appearance.
4. Dark green-colored leaves.
5. Freely flowering habit.
6 Compact and dense inflorescences with numerous coral red-colored flowers.
7. Good garden performance.

Plants of the new *Agastache* can be compared to plants of the parent selection. In side-by-side comparisons, plants of the new *Agastache* differ primarily from plants of the parent selection in the following characteristics:

1. Plants of the new *Agastache* are more vigorous than plants of the parent selection.
2. Plants of the new *Agastache* flower slightly later than plants of the parent selection.
3. Flowers of plants of the new *Agastache* are darker coral red in color than flowers of plants of the parent selection.
4. Plants of the new *Agastache* have not been observed to produce seeds whereas plants of the parent selection have been observed to produce seeds.

Plants of the new *Agastache* can be compared to plants of *Agastache* spp. 'Rosie Posie', disclosed in U.S. Pat. No. 25,857. In side-by-side comparisons, plants of the new *Agastache* differ primarily from plants of 'Rosie Posie' in the following characteristics:

1. Plants of the new *Agastache* are more compact than plants of 'Rosie Posie'.
2. Plants of the new *Agastache* are more freely branching and denser than plants of 'Rosie Posie'.
3. Plants of the new *Agastache* flower three to five days earlier than plants of 'Rosie Posie'.
4. Flowers of plants of the new *Agastache* are lighter coral red in color than flowers of plants of 'Rosie Posie'.
5. Plants of the new *Agastache* have not been observed to produce seeds whereas plants of 'Rosie Posie' have been observed to produce seeds.

Plants of the new *Agastache* can also be compared to plants of *Agastache* hybrid 'Kudos Coral', disclosed in U.S. Pat. No. 25,613. In side-by-side comparisons, plants of the new *Agastache* differ primarily from plants of 'Kudos Coral' in the following characteristics:

1. Plants of the new *Agastache* are more vigorous than plants of 'Kudos Coral'.
2. Plants of the new *Agastache* flower three to five days later than plants of 'Kudos Coral'.
3. Flowers of plants of the new *Agastache* are coral red in color whereas flowers of plants of 'Kudos Coral' are more coral orange in color.
4. Plants of the new *Agastache* have not been observed to produce seeds whereas plants of 'Kudos Coral' have been observed to produce seeds.

BRIEF DESCRIPTION OF THE PHOTOGRAPHS

The accompanying colored photographs illustrate the overall appearance of the new *Agastache* plant showing the colors as true as it is reasonably possible to obtain in colored reproductions of this type. Colors in the photographs may differ slightly from the color values cited in the detailed botanical description which accurately describe the actual colors of the new *Agastache* plant.

The photograph on the first sheet (FIG. 1) is a side perspective view of a typical flowering plant of 'G19131' grown in a container.

Figure 2:
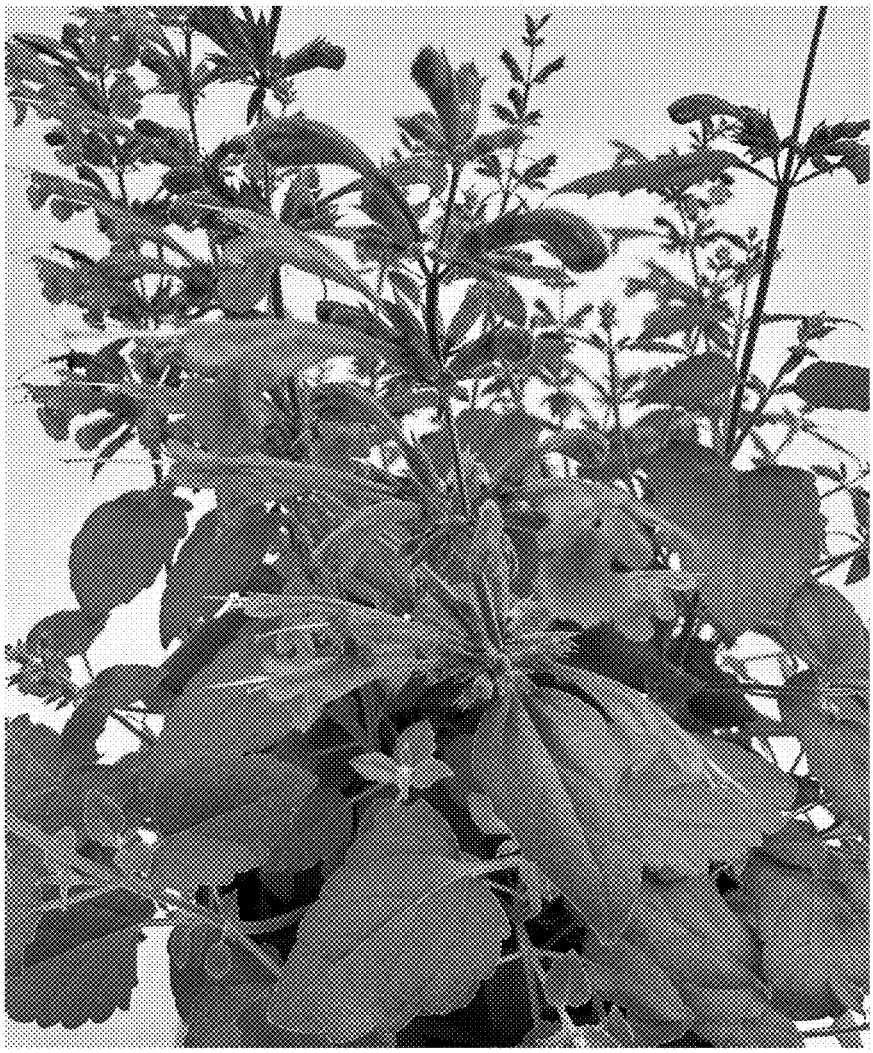

The photograph on the second sheet (FIG. 2) is a close-up view of a typical flowering plant of 'G19131'.

DETAILED BOTANICAL DESCRIPTION

The aforementioned photographs and following observations and measurements describe plants grown during the late winter and early spring in 10.75-cm containers in a glass-covered greenhouse in Loudon, New Hampshire and under cultural practices typical of commercial *Agastache* production. During the production of the plants, day and night temperatures averaged 20° C. Plants were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Agastache hybrida* 'G19131'.

Parentage:

*Female, or seed, parent.*—Proprietary selection of *Agastache hybrida* identified as code number 50867-1, not patented.

*Male, or pollen, parent.*—Proprietary selection of *Agastache hybrida* identified as code number 50867-1, not patented.

Propagation:

*Type.*—By vegetative cuttings.

*Time to initiate roots, summer and winter.*—About 10 to 14 days at soil temperatures about 22.2° C. and ambient temperatures about 18.3° C.

*Time to produce a rooted young plant from an unrooted cutting, summer and winter.*—About five to six weeks at soil temperatures about 22.2° C. and ambient temperatures about 18.3° C.

*Root description.*—Medium in thickness and fibrous; typically white to creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; relatively compact, broadly upright to somewhat outwardly spreading plant habit; vigorous growth habit and rapid growth rate; freely branching habit; dense and bushy appearance.

*Branching habit.*—Freely basal branching with numerous primary lateral branches; secondary branches potentially developing at every node; pinching enhances lateral branch development.

*Plant height, soil level to top of foliar plane.*—About 16 cm to 18 cm.

*Plant height, soil level to top of floral plane.*—About 20 cm to 22 cm.

*Plant width.*—About 28 cm to 32 cm.

*Primary branch description.*—Length (excluding inflorescence): About 15 cm to 20 cm. Diameter: About 2 mm to 2.5 mm. Internode length: About 2.7 cm to 3.5 cm. Shape: Quadrangular. Strength: Strong, not flexible. Aspect: Erect to about 25° to 30° from vertical. Texture and luster: Smooth, glabrous; slightly glossy. Fragrance: Moderately fragrant; pungent yet pleasant. Color, developing: Close to 144A. Color, developed: Close to between 144A and 146A variably overlain with close to 59A.

Leaf description:

*Arrangement.*—Opposite and decussate; simple.

*Length.*—About 3.8 cm to 4.2 cm.

*Width.*—About 3.2 cm to 3.5 cm.

*Shape.*—Ovate to cordate.

*Apex.*—Acute.

*Base.*—Cordate.

*Margin.*—Crenate with medium indentations.

*Texture and luster, upper and lower surfaces.*—Smooth, glabrous; velvety; matte.

*Venation pattern.*—Pinnate and reticulate.

*Color.*—Developing leaves, upper surface: Close to NN137A. Developing leaves, lower surface: Close to NN137B underlain with close to N79A. Fully expanded leaves, upper surface: Close to NN137A; venation, close to 146A. Fully expanded leaves, lower surface: Close to 147B; venation, close to 147B.

*Petioles.*—Length: About 1.8 cm to 2 cm. Diameter: About 1.5 mm to 2 mm. Strength: Moderately strong; flexible. Texture and luster, upper and lower surfaces: Smooth, glabrous; somewhat glossy. Color, upper and lower surfaces: Close to 144A.

Flower description:

*Flower arrangement and shape*.—Single bilabiate flowers arranged on erect and relatively compact and dense spikes; freely flowering habit with about 25 to 30 flowers developing per terminal inflorescence; numerous terminal and axillary inflorescences with flowers developing continuously per plant during the flowering season; flowers face initially upright to mostly outwardly with development.

*Fragrance*.—Slightly fragrant; pleasant and sweet.

*Natural flowering season*.—Early flowering habit, depending on temperature, plants begin flowering about seven to eight weeks after planting rooted young plants; plants flower from spring until the autumn in an outdoor environment in Pennsylvania; petals not persistent and sepals persistent.

*Flower buds*.—Length: About 6 mm to 7.5 mm. Diameter: About 1 mm. Shape: Elongated tubular. Texture and luster: Smooth, glabrous; matte. Color: Close to 144A variably overlain with close to 59A.

*Inflorescence height*.—About 10 cm to 12 cm.

*Inflorescence diameter*.—About 4.5 cm to 5 cm.

*Flower size*.—About 6 mm by 8 mm.

*Flower depth*.—About 2.8 cm to 3.2 cm.

*Flower throat diameter*.—About 3 mm to 4 mm.

*Flower tube length*.—About 2.2 cm to 2.5 cm.

*Flower tube diameter, proximally*.—About 1 mm to 1.5 mm.

*Petals*.—Arrangement: Five petals; two fused upper petals (upper lip) with two lateral petals and one lower petal (lower lip); petals fused towards the base. Upper lip: Length: About 5 mm. Width: About 4 mm. Lateral petals: Length: About 2 mm. Width: About 3 mm. Lower lip: Length: About 4 mm. Width: About 6 mm. All petal lobes: Shape: Roughly spatulate. Apex: Obtuse. Base: Fused. Margin: Entire; not undulate. Texture and luster, upper surface: Smooth, glabrous; matte. Texture and luster, lower surface: Smooth, glabrous; slightly glossy. Color: When developing and fully developed, upper surface: Close to between 55B and N66C; under higher light conditions, color becoming closer to between 48A and 51A; venation, similar to lamina colors; colors do not change with subsequent development. When developing and fully developed, lower surface: Close to between 55B and N66C; under higher light conditions, color becoming closer to between 48A and 51A; venation, similar to lamina colors; colors do not change with subsequent development. Throat, texture and luster: Smooth, glabrous; matte. Throat color: Close to 10C. Tube, texture and luster: Smooth, glabrous; slightly glossy. Tube color: Close to between 55B and N66C; under higher light conditions, color becoming closer to between 48A and 51A.

*Calyx*.—Arrangement: Five sepals fused to form a tubular calyx. Length: About 8 mm. Width: About 2 mm. Sepal length: About 8 mm. Sepal width: About 1 mm. Sepal shape: Roughly linear; fused. Sepal apex: Acuminate. Sepal margin, free part: Entire. Sepal texture and luster, upper surface: Smooth, glabrous; slightly glossy. Sepal texture and luster, lower surface: Smooth, glabrous; matte. Sepal color: When opening, upper and lower surfaces: Close to 154D. Fully opened, upper and lower surfaces: Close to 144B.

*Pedicels*.—Length: About 2 mm to 3 mm. Diameter: About 0.5 mm to 1 mm. Strength: Strong, wiry; flexible. Aspect: About 45° from peduncle axis. Texture and luster: Smooth, glabrous; somewhat glossy. Color: Close to 144A.

*Reproductive organs*.—Stamens: Quantity per flower: Four. Filament length: About 2.2 cm to 2.4 cm. Filament color: Close to 50C. Anther shape: Rounded. Anther size: About 1 mm by 1 mm. Anther color: Close to 77A. Pollen amount: None observed. Pistils: Quantity per flower: One. Pistil length: About 2.4 cm. Stigma diameter: About 0.5 mm. Stigma shape: Cleft. Stigma color: Close to N144A. Style length: About 2.2 cm. Style color: Close to 145A to 145B. Ovary color: Close to 154D.

*Seeds and fruits*.—To date, seed and fruit production has not been observed on plants of the new *Agastache*.

Pathogen & pest resistance: To date, plants of the new *Agastache* have not been noted to be resistant to pathogens and pests common to *Agastache* plants.

Garden performance: Plants of the new *Agastache* have exhibited good garden performance, to tolerate temperatures ranging from 13° C. to about 38° C.

It is claimed:

1. A new and distinct *Agastache* plant named 'G19131' as herein illustrated and described.

* * * * *